United States Patent [19]

Michaux et al.

[11] 4,018,843
[45] Apr. 19, 1977

[54] PROCESS FOR THE OBTAINING OF ISOBUTYLENE OF HIGH PURITY

[75] Inventors: Jean-Pierre Michaux, Chatou; Guy Arnaud, Le Havre, both of France

[73] Assignee: Compagnie Francaise de Raffinage, Paris, France

[22] Filed: May 4, 1976

[21] Appl. No.: 683,178

[30] Foreign Application Priority Data

May 9, 1975 France ............................ 75.14589

[52] U.S. Cl. .............................. 260/677 A; 203/42; 203/73
[51] Int. Cl.[2] ..................... C07C 7/04; C07C 11/08
[58] Field of Search ............ 260/677 A; 203/42, 73

[56] References Cited

UNITED STATES PATENTS

| | | | |
|---|---|---|---|
| 3,657,374 | 4/1972 | Schloemer et al. | 260/677 A |
| 3,794,690 | 2/1974 | Steggerda | 260/677 A |
| 3,864,419 | 2/1975 | Murphy | 260/677 A |

*Primary Examiner*—C. Davis
*Attorney, Agent, or Firm*—Curtis, Morris & Safford

[57] ABSTRACT

A process for obtaining isobutylene in a purity greater than 99.5% from an initial feed of relatively pure isobutylene which further has minor quantities of tertiary butyl alcohol, water, polymers of isobutylene, and cis and trans-2-butenes in an economic manner while retaining good yields of the isobutylene by distilling the initial feed to separate a significant portion of the isobutylene with a purity equal to or greater than 99.5% with the remaining mixture containing tertiary butyl alcohol, water, polymers of isobutylene, cis and trans-2-butenes and isobutylene in an amount from 0 to 5% by weight; washing the latter mixture with water to obtain an aqueous phase of tertiary butyl alcohol and an organic phase containing the remainder of said mixture including the isobutylene not previously separated (and some tertiary butyl alcohol not dissolved in the wash water); and distilling the organic phase to separate the polymers of isobutylene from a mixture containing isobutylene and the cis and trans-2-butenes whereby the latter can be recovered by recycling for extraction; and distilling the aqueous phase to separate an azeotrope from the remainder of the water whereby the tertiary butyl alcohol in the azeotrope may be dehydrated to isobutylene.

8 Claims, 1 Drawing Figure

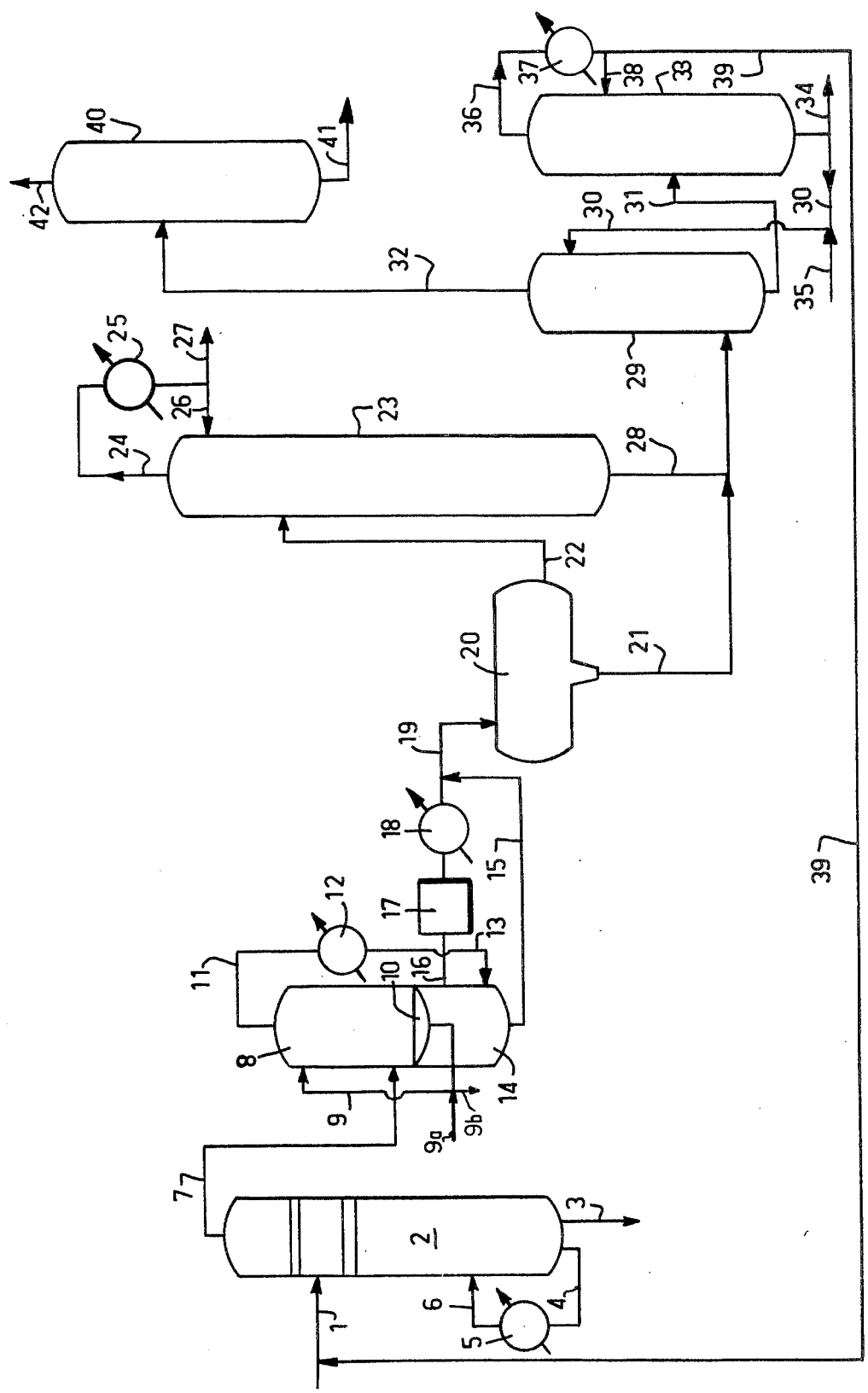

PROCESS FOR THE OBTAINING OF ISOBUTYLENE OF HIGH PURITY

The present invention relates to a method of obtaining isobutylene of a purity of more than 99.5% from a feed of isobutylene containing impurities. More particularly it concerns a process of treating the isobutylene obtained in a process for the extraction of isobutylene with sulfuric acid.

It is known that isobutylene can be selectively extracted from a mixture of hydrocarbons containing four carbon atoms whose boiling point is close to that of the isobutylene. The applicants' assignee has developed a process in which the extraction agent is sulfuric acid in a concentration close to 50%. This process provides the great advantage of permitting the extraction and regeneration of the isobutylene with an acid of constant concentration and thus avoids successive dilutions and reconcentrations of the sulfuric acid. This process is described in CHEMICAL ENGINEERING PROGRESS - Volume 61 - No. 3 — Pages 77 to 80 (March, 1965) and forms the subject of U.S. Pat. Nos. 3,005,856 and 3,073,874.

The efflux which comes from the regeneration of the isobutylene if formed primarily of isobutylene, but it also contains tertiary butyl alcohol and, in lesser quantities, polymers of isobutylene, water, and possibly sulfuric acid. The tertiary butyl alcohol comes from an incomplete regeneration of the isobutylene. The isobutylene polymers consist primarily of lower polymers — dimers and trimers. The possible presence of traces of sulfuric acid is due to the entrainment by the gaseous isobutylene of droplets of the acid solution subjected to the regeneration of the isobutylene.

The simplest method of treating this efflux is to introduce it into a soda scrubbing tower so as to eliminate the traces of sulfuric acid and then separate the isobutylene on the one hand and a mixture of tertiary butyl alcohol, lower polymers of isobutylene and water, on the other hand. The isobutylene is taken up in a compressor and then purified by distillation. The polymers are separated from the tertiary butyl alcohol by washing with water.

The mixture of tertiary butyl alcohol, polymers and water, separated from the isobutylene, now contains dissolved isobutylene in a quantity of the order of 10% by weight of this mixture and of the order of 1% by weight of the isobutylene to be regenerated. In order to recover practically all of the isobutylene contained in the efflux of the regeneration and in particular the traces of isobutylene contained in the mixture of tertiary butyl alcohol, isobutylene polymers, and water (which is separated from the crude isobutylene after washing with an alkaline solution), the mixture described above and the crude isobutylene (after liquefaction of the latter) can be allowed to settle out. This thus separates into on the one hand an organic phase formed of all of the regenerated isobutylene, the tertiary butyl alcohol, and the isobutylene polymers and, on the other hand, an aqueous phase containing tertiary butyl alcohol. The isobutylene is obtained by distillation of the organic phase. This improvement forms the subject of U.S. Pat. No. 3,794,690, owned by the applicants' assignee.

The method of treating the efflux from the regeneration of isobutylene, with or without the improvement described above, makes it possible to recover isobutylene of a purity substantially equal to 99.5%.

Although this purity is in itself very high, it is sometimes necessary, for some uses, to have isobutylene of even greater purity. This is true, in particular, when the isobutylene is used as a polymerization monomer for the manufacture of butyl rubber. The use of isobutylene of greater purity facilitates, on the one hand, the polymerization reaction and, on the other hand, makes it possible to reduce the cost of the process by decreasing the quantity of products to be recycled to the inlet of the extraction unit.

Among the impurities contained in the crude isobutylene coming from the regeneration, cis-2-butene and trans-2-butene are very difficult to separate by distillation from the isobutylene, as shown in the following table I in which the boiling points at atmospheric pressure are shown.

TABLE I

| Isobutylene | − 6.9° C |
|---|---|
| Trans-2-butene | + 0.88° C |
| Cis-2-butene | + 3.7° C |

With the use of a distillation column of very high efficiency, it is possible to separate the isobutylene from the 2-butenes. While this makes it possible to obtain isobutylene of very high purity, it also results in a decrease in the yield of isobutylene, a part thereof being entrained with the 2-butenes.

An object of the present invention is economically to obtain isobutylene of very high purity, while recovering all the isobutylene, under economic conditions.

Therefore a preferred embodiment of the present invention is a process of obtaining isobutylene of a purity of more than 99.5%, starting from an initial feed comprising a major proportion of isobutylene and a minor proportion of tertiary butyl alcohol, water, polymers of isobutylene, and cis-and trans-2-butenes, said process being characterized by the fact that it comprises the following steps:

A. separating by distillation, on the one hand, isobutylene of a purity equal to or greater than 99.5% and, on the other hand, a mixture containing tertiary butyl alcohol, water, polymers of isobutylene, cis- and trans-2-butenes, and isobutylene in such amount that it represents from 0 to 15% by weight of the isobutylene contained in the initial feed;

B. washing the mixture obtained in the preceding stage with water, said washing making it possible to obtain on the one hand, an aqueous phase containing tertiary butyl alcohol and, on the other hand, an organic phase containing the polymers of the isobutylene, the cis- and trans-2-butenes, the isobutylene not separated in step (A), and the butyl alcohol which has not dissolved in the wash water;

C. separating by distillation from the organic phase obtained in step (B), on the one hand, isobutylene polymers containing small amounts of tertiary butyl alcohol and, on the other hand, a mixture containing isobutylene and cis- and trans-2-butenes containing small amounts of other hydrocarbons having four carbon atoms, the isobutylene contained in said mixture being capable of recovery by extraction;

D. separating by distillation from the aqueous phase obtained in step (B), on the one hand water, and, on the other hand, the azeotrope consisting of tertiary butyl alcohol and water, the tertiary butyl alcohol contained in the azeotrope being capable of being dehydrated to lead to isobutylene.

Another preferred embodiment of the present invention consists of applying the process described above to the treatment of a feed whose composition by weight is as follows: isobutylene from 50 to 100%, tertiary butyl alcohol from 0 to 30%, cis- and trans-2-butenes from 0 to 2%, 1-butene and other hydrocarbons having 3 or 4 carbon atoms from 0 to 0.5%, polymers of isobutylene from 0 to 10%, water from 0 to 75%, said feed being obtained in the following manner:

a. treatment with sulfuric acid of a concentration of close to 50% under conditions for the selective extraction of isobutylene, of a mixture of hydrocarbons having four carbon atoms whose boiling point is close to that of isobutylene, b. regeneration of the crude isobutylene from the extract obtained, c. washing the crude isobutylene with an alkaline solution;

said application being characterized by the fact that:
— the mixture of isobutylene and 2-butenes obtained in step (C) of the process described above is recycled into the batch of the isobutylene selective extraction step mentioned under (a);
— the tertiary-butyl-alcohol/water azeotrope which has been separated in step (D) of the process described above is recycled into the feed of the step for the regeneration of the isobutylene mentioned under (b).

The effectiveness of the distillation column intended to separate the isobutylene from the mixture of tertiary butyl alcohol, water, isobutylene polymers, and 2-butenes can be selected as a function of the purity desired for the isobutylene. As an increase in his effectiveness requires an increased expenditure for apparatus and energy, it is important to adapt it to the purity desired for the isobutylene.

The amounts of tertiary butyl alcohol, water, and isobutylene polymers contained in the feed are not critical, the boiling points of these substances being sufficiently different from that of isobutylene for them to be separated therefrom, without difficulty by means of the distillation column necessary to separate the isobutylene and the 2-butenes. This is not true with respect to the amount of 2-butenes. In order to avoid having to use a distillation column having a very high number of plates and therefore requiring a large expenditure of energy it is preferable to carry out the extraction referred to under (a) under conditions of selectivity such that the amount of 2-butenes contained in the feed, calculated with reference to the isobutylene, is equal to or less than 2% by weight.

The feed may also contain hydrocarbons having 4 carbon atoms and less, such as propylene, isobutane, normal butane, 1-butene, and 1,3-butadiene. These hydrocarbons, which have boiling points less than or close to that of isobutylene, are collected with the latter upon its separation from the 2-butenes. It is therefore necessary that the amount of these impurities contained in the feed, calculated with reference to the isobutylene, be less than 0.5% by weight if it is desired to obtain isobutylene of a purity of more than 99.5%; this condition is satisfied by effecting the extraction mentioned under (a) selectively.

In the particularly interesting application of the process in accordance with the invention which consists of treating a feed of isobutylene resulting from the extraction of isobutylene from a mixture of hydrocarbons having four carbon atoms by a solution of sulfuric acid of a concentration of close to 50%, the mixture of 2-butenes and isobutylene obtained in the step of the separation of the polymers is recycled into the feed of the isobutylene extraction stage on the one hand and the azeotrope consisting of the tertiary butyl alcohol and water is recycled into the feed of the stage for the regeneration of isobutylene from the extract on the other hand, the alcohol being dehydrated by sulfuric acid to form isobutylene.

The sole FIGURE attached to the present specification is a simplified diagram showing, by way of illustration and not of limitation, the application of the process of the invention to the treatment of a feed of crude isobutylene coming from the extraction of isobutylene from a mixture of hydrocarbons by a solution of sulfuric acid of a concentration close to 50%.

In accordance with this FIGURE, the extract coming from a unit (not shown) for the extraction of isobutylene from a cut containing hydrocarbons with four carbon atoms by a solution of sulfuric acid of a concentration close to 50% is introduced, via the line 1, into the upper portion of a regeneration column 2. This extract contains essentially, in addition to the isobutylene absorbed by the sulfuric acid solution, tertiary butyl alcohol, polymers of isobutylene, and 2-butenes. The regeneration column consists of a plate column. The pressure of the column is close to atmospheric pressure, the top and bottom temperatures of the column being equal to about 50° C and 130° C respectively.

In this column, the isobutylene is desorbed from the acid solution, a part of which is collected at the bottom of the column by the line 3 and recycled to the extraction unit. The other part, collected by the line 4, is reheated in the reheater 5 and introduced again into the column via the line 6.

At the top of the column there is collected, via the line 7, a mixture formed essentially of isobutylene, polymers thereof, tertiary butyl alcohol, butenes, sulfuric acid, and water. In order to eliminate the traces of sulfuric acid, this mixture is introduced into a soda wahsing device 8. The soda solution is recycled through the line 9, possibly equipped with a make-up 9a and a purge 9b. The vapors are collected by the line 11 and the liquid is collected at 10.

The vapors collected by the line 11 are condensed partially in the condenser 12 and introduced via the line 13 into the separation enclosure 14. The isobutylene vapors, separated from a liquid phase (collected by the line 15), are conducted via the line 16 to a compressor 17 and then to a condenser 18. At the outlet from the condenser 18, the liquid isobutylene is mixed with the liquid phase coming from the enclosure 14 via the line 15. The mixture is introduced, via line 19, into a settling tank 20, from which there are extracted, via line 21, an aqueous phase containing the major part of the water and of the tertiary butyl alcohol and, via the line 22, an organic phase containing the isobutylene, small quantities of hydrocarbons having four carbon atoms including 2-butenes, isobutylene polymers as well as tertiary butyl alcohol and water.

The organic phase is introduced, via the line 22, into the upper portion of a distillation column 23. This column, which has an effectiveness of about 40 to 50 theroretical plates, operates with a reflux ratio of between 5 and 10. The pressure of the column is between about 3 and 8 bars, the temperatures at the top and bottom of the column being between about 30° and 60° C, on the one hand, and about 100° and 150° C, on the other hand, respectively. However, it is preferably not to exceed a temperature of about 130° C at the bottom of the column.

The fraction emerging from the head of the column 23 via the line 24 is condensed in the condenser 25. A portion of this fraction is recycled via the line 26 into the column 23. The other portion, collected by the line 27, consists of isobutylene of a purity of more than 99.90%. The fraction emerging at the bottom of the column 23 via the line 28 is formed primarily of tertiary butyl alcohol, water, isobutylene polymers, 2-butenes, and isobutylene representing about 2% by weight of the isobutylene introduced into the column 23. This fraction is led to the lower portion of a column 29 where it is extracted in countercurrent with water. The water is introduced by the line 30 into the upper portion of the column 29.

The extraction takes place at a temperature of about 40° C. The tertiary butyl alcohol is extracted by the water and the mixture of water and alcohol is collected at the bottom of the column 29 by the line 31.

A mixture, formed primarily of isobutylene, 2-butenes, and isobutylene polymers is collected at the top of the column 29 by the line 32.

The mixture of water and tertiary butyl alcohol is conducted by the line 31 into the central portion of the distillation column 33. This column operates under a pressure substantially equal to atmospheric pressure. The operating parameters can be easily determined by the man skilled in the art.

The water which has collected at the bottom of the column 33 is recycled to column 29 via the line 30. This line may be equipped with a purge 34 and a make-up 35.

The mixture, consisting primarily of water and tertiary butyl alcohol which has collected at the bottom of the settling tank 20 is conducted via the line 21 to the extraction column 29.

The fraction emerging from the top column 33 is formed of the azeotrope of tertiary butyl alcohol and water. This fraction, collected by the line 36, is cooled in the condenser 37. A part of the azeotrope is reintroduced into the column via the line 38, while the balance is recycled to the feed of the regeneration column, via the line 39. At the regeneration stage, the tertiary butyl alcohol contained in the azeotrope is dehydrated to from isobutylene.

The mixture collected at the top of the column 29 by the line 32 is conducted into the central portion of a distillation column 40. The pressure of the column is, for instance, close to five atmospheres. The operating parameters can be easily determined by the man skilled in the art.

At the bottom of the column, the stabilized polymers of isobutylene are collected primarily via the line 41. The fraction collected at the top of the column is formed primarily of isobutylene and 2-butenes and is recycled, via the line 42, to the feed of the extraction unit, not shown.

The invention is also illustrated by the following example, which is given solely by way of illustration and not of limitation.

EXAMPLE

This example concerns the treatment of a feed by a process similar to that shown in the accompanying figure. The reference numbers are those contained in said FIGURE.

In this example, the principal operating parameters of the columns are as follows:
COLUMN 23:
  Pressure 5 to 6 atmospheres
  top temperature 45° C
  bottom temperature 127° C
  number of theoretical plates: 48 (not including reheater and condenser)
  temperature of the batch: 38° C
  reflux ratio: 5.4
COLUMN 33:
  pressure: atmospheric
  top temperature about 80° C
  bottom temperature about 100° C
COLUMN 40:
  pressure 5 atmospheres
  top temperature about 40° C
  bottom temperature about 150° C The compositions of the feed introduced via the line 22 into column 23 and of the mixtures collected by the lines 27 and 28 are indicated in Table II below.

TABLE II

|  | line 22 | line 27 | | line 28 | |
| --- | --- | --- | --- | --- | --- |
|  | % by weight | weight in g | % by weight | weight in g | % by weight |
| hydrocarbons having 3 carbon atoms and isobutane | 0,008 | 0,008 | 0,010 |  |  |
| normal butane | 0,004 | 0,001 | 0,001 | 0,003 | 0,014 |
| 1-butene | 0,028 | 0,028 | 0,035 |  | 0,002 |
| isobutene | 80,076 | 78,469 | 99,916 | 1,607 | 7,487 |
| butadiene | 0,004 | 0,004 | 0,005 |  | <0.001 |
| trans-2-butene | 0,180 | 0,023 | 0,029 | 0,157 | 0,733 |
| cis-2-butene | 0,150 | 0,003 | 0,004 | 0,147 | 0,685 |
| tertiary butyl alcohol | 13,000 |  |  | 13,000 | 60,565 |
| isobutylene polymers | 4,050 |  |  | 4,050 | 18,868 |
| water | 2,500 |  |  | 2,500 | 11,646 |
|  | 100,000 | 78,536 | 100,000 | 21,464 | 100,000 |

Table II makes it possible to note that:
a. the isobutylene collected by line 27 has a purity of 99.9%;
b. the mixture collected by line 28 contains 7.47% by weight of isobutylene, representing about 2% by weight of the charge introduced through the line 22;
c. the feed introduced through the line 22 contains 80.450 g of hydrocarbons having 4 and fewer carbon atoms, including 80.076 g of isobutylene. In the case of a conventional treatment of this feed, customarily carried out with a column of about 26 actual plates, all the isobutylene of the feed is collected at the top of the column, but this isobutylene contains all the other hydrocarbons having four and fewer carbon atoms and in particular all of the 2-butenes. This isobutylene therefore has a purity of only $$\frac{80.076 \times 100}{80.450} = 99.5\%$$

d. the process of the invention therefore makes it possible to recover an isobutylene of a purity greater than 99.9%.

We claim:

1. A process for obtaining isobutylene of a purity greater than 99.5% with good yield and efficiency from an initial feed comprising a major quantity of isobutylene and a minor quantity of tertiary butyl alcohol, water, polymers of isobutylene, and cis- and trans-2-butenes, said process comprising the following stages:
   A. separating by distillation, on the one hand, isobutylene of a purity equal to or greater than 99.5%, and on the other hand, a mixture containing tertiary butyl alcohol, water, polymers of isobtylene, cis- and trans-2-butenes and isobutylene in such amount that it represents from 0 to 15% by weight of the isobutylene contained in the initial feed;
   B. washing the mixture obtained in the stage (A) with water to obtain, on the one hand, an aqueous phase containing tertiary butyl alcohol and, on the other hand, an organic phase containing the isobutylene polymers, the cis- and trans-2-butenes, the isobutylene not separated in stage (A), and the tertiary butyl alcohol not dissolved in the wash water;
   C. distilling the organic phase from stage (B), to separate the polymers of isobutylene from a mixture containing isobutylene and the cis- and trans-2-butenes, whereby the isobutylene contained in said resulting mixture is capable of recovery by extraction;
   D. distilling the aqueous phase from stage (B), to separate water from an azeotrope of tertiary butyl alcohol and water, whereby the tertiary butyl alcohol in the azeptrope is capable of being dehydrated to isobutylene.

2. A process according to claim 1 wherein the initial feed has a content of 2-butenes, calculated with reference to the isobutylene, which is equal to or less than 2% by weight.

3. A process according to claim 1, wherein the initial feed has a content of hydrocarbons having four and fewer carbon atoms, other than isobutylene and the 2-butenes, calculated with reference to the isobutylene which is equal to or less than 0.5% by weight.

4. A process according to claim 2, wherein the initial feed has a content of hydrocarbons having four and fewer carbon atoms, other than isobutylene and the 2-butenes, calculated with reference to the isobutylene which is equal to or less than 0.5% by weight.

5. The application of the process according to claim 1 to the treatment of a feed having the following composition by weight: isobutylene, 50 to 100%; tertiary butyl alcohol, 0 to 30%; cis- and trans-2-butenes, 0 to 2%; 1-butene and other C3 and C4 hydrocarbons from 0 to 0.5%; isobutylene polymers, 0 to 10%; water, 0 to 15%; said feed being obtained by a method comprising the following stages:
   a. treatment with sulfuric acid of a concentration of close to 50%, under selective isobutylene extraction conditions, of a mixture of hydrocarbons having four carbon atoms whose boiling point is close to that of isobutylene;
   b. regeneration of the crude isobutylene from the extract obtained;
   c. washing of the crude isobutylene by means of an alkaline solution;
   said application comprising the further steps of:
   — recycling the mixture of isobutylene and of 2-butenes obtained in stage (C) of claim 1 into the feed of the isobutylene selective extraction of stage (a);
   — recycling the azeotrope of tertiary butyl alcohol and water from stage (D) of claim 1 into the feed of the isobutylene regeneration stage (b).

6. The application of the process according to claim 2 to the treatment of a feed having the following composition by weight: isobutylene, 50 to 100%; tertiary butyl alcohol, 0 to 30%; cis- and trans-2-butenes, 0 to 2%; 1-butene and other C3 and C4 hydrocarbons from 0 to 0.5%; isobutylene polymers, 0 to 10%; water, 0 to 15%; said feed being obtained by a method comprising the following stages:
   a. treatment with sulfuric acid of a concentration of close to 50%, under selective isobutylene extraction conditions, of a mixture of hydrocarbons having four carbon atoms whose boiling point is close to that of isobutylene;
   b. regeneration of the crude isobutylene from the extract obtained;
   c. washing of the crude isobutylene by means of an alkaline solution;
   said application comprising the further steps of:
   — recycling the mixture of isobutylene and of 2-butenes obtained in stage (C) of claim 1 into the feed of the isobutylene selective extraction of stage (a);
   — recycling the azeotrope of tertiary butyl alcohol and water from stage (D) of claim 1 into the feed of the isobutylene regeneration stage (b).

7. The application of the process according to claim 3 to the treatment of a feed having the following composition by weight: isobutylene, 50 to 100%; tertiary butyl alcohol, 0 to 30%; cis- and trans-2-butenes, 0 to 2%; 1-butene and other C3 and C4 hydrocarbons from 0 to 0.5%; isobutylene polymers, 0 to 10%; water, 0 to 15%; said feed being obtained by a method comprising the following stages:
   a. treatment with sulfuric acid of a concentration of close to 50%, under selective isobutylene extraction conditions, of a mixture of hydrocarbons having four carbon atoms whose boiling point is close to that of isobutylene;
   b. regeneration of the crude isobutylene from the extract obtained;
   c. washing of the crude isobutylene by means of an alkaline solution;
   said application comprising the further steps of:
   — recycling the mixture of isobutylene and of 2-butenes obtained in stage (C) of claim 1 into the feed of the isobutylene selective extraction of stage (a);
   — recycling the azeotrope of tertiary butyl alcohol and water from stage (D) of claim 1 into the feed of the isobutylene regeneration stage (b).

8. The application of the process according to claim 4 to the treatment of a feed having the following composition by weight: isobutylene, 50 to 100%; tertiary butyl alcohol, 0 to 30%; cis- and trans-2-butenes, 0 to 2%; 1-butene and other C3 and C4 hydrocarbons from 0 to 0.5%; isobutylene polymers, 0 to 10%; water, 0 to 15%; said feed being obtained by a method comprising the following stages:
- a. treatment with sulfuric acid of a concentration of close to 50%, under selective isobutylene extraction condtitions, of a mixture of hydrocarbons having four carbon atoms whose boiling point is close to that of isobutylene;
- b. regeneration of the crude isobutylene from the extract obtained;
- c. washing of the crude isobutylene by means of an alkaline solution;

said application comprising the further steps of:
- — recycling the mixture of isobutylene and of 2-butenes obtained in stage (C) of claim 1 into the feed of the isobutylene selective extraction of stage (a);
- — recycling the azeotrope of tertiary butyl alcohol and water from stage (D) of claim 1 into the feed of the isobutylene regeneration stage (b).

* * * * *